United States Patent [19]

Sugimoto

[11] Patent Number: 4,542,519
[45] Date of Patent: Sep. 17, 1985

[54] COMPUTERIZED TOMOGRAPHY APPARATUS

[75] Inventor: Hiroshi Sugimoto, Tochigi, Japan

[73] Assignee: Tokyo Shibaura Denki Kabushiki Kaisha, Kawasaki, Japan

[21] Appl. No.: 462,431

[22] Filed: Jan. 31, 1983

[30] Foreign Application Priority Data

Feb. 1, 1982 [JP] Japan .................................. 57-13295

[51] Int. Cl.$^4$ ............................................ G03B 41/16
[52] U.S. Cl. ...................................... 378/19; 250/366
[58] Field of Search ...................... 378/19, 4; 250/366, 250/367

[56] References Cited

U.S. PATENT DOCUMENTS

| | | | |
|---|---|---|---|
| 4,110,621 | 8/1978 | Horn | 250/361 R |
| 4,220,860 | 9/1980 | Carlson et al. | 250/361 R |
| 4,234,792 | 11/1980 | DeCou | 250/361 R |
| 4,363,969 | 12/1982 | Ong | 378/19 |
| 4,414,473 | 11/1983 | Hoffman | 378/19 |

*Primary Examiner*—Craig E. Church
*Attorney, Agent, or Firm*—Oblon, Fisher, Spivak, McClelland & Maier

[57] ABSTRACT

A computerized tomography apparatus including an array of radiation detectors including plural scintillation crystals and photoelectric transducers alternately disposed to receive a fan shaped radiation beam. The scintillation crystal is optically connected with the photoelectric transducer at the interface therebetween, which is elongated in the direction of a radiation impinging thereon and transverse the direction of the array. The radiation passing through a patient's body to be examined impinges on the crystals causing them to scintillate. The light scintillated strikes the detection region of the photoelectric transducer causing the photoelectric effect to be manifested. The detection region does not depend on the size of radiation incident surface of the crystal. A certain portion of the light reaches the detection region in a shorter path. The photoelectric transducer produces an electrical signal related to the intensity of the incident radiation as result of impinging light scintillated by the crystals.

3 Claims, 3 Drawing Figures

COMPUTERIZED TOMOGRAPHY APPARATUS

BACKGROUND OF THE INVENTION

1. Field of the Invention

This invention relates to a computerized tomography apparatus and more particularly to a computerized tomography apparatus having a relative large number of radiation detectors to produce output signals for developing an image representing a two dimensional slice through a patient's body.

2. Description of the Prior Art

In such an apparatus as above noted, a radiation source rotates around the patient within a selected plane and a fan-shaped beam is irradiated through the patient at many different views so that the beam passes through the slice specified by the plane. The x-rays of different paths through that slice are absorbed to a greater or lesser degree depending on the absorbitities of the patient's tissue through which the x-rays pass. The intensities of the x-rays emerging from the body represent the absorption coefficiencies integrated along the paths followed by the x-rays. An array of detectors positioned opposite the fan beam source beyond the patient's body measures the intensity of the emerging radiation and produces output signals corresponding to the measured radiation intensities. These signals are processed by a reconstruction unit such as a device described, for example, in U.S. Pat. Nos. 4,149,249 and 4,351,247 to produce rapidly a two dimensional image of the body slice.

Normally each detector includes a scintillation crystal upon which radiation impinges. A radiation photon causes the scintillation crystal to luminescence with an intensity related to the intensity of the radiation. The light resulting from the luminescence diverges in all directions. A portion of the light experiences a reflection against a reflection layer surrounding the side wall of the crystal and descends toward the bottom of the crystal. Each detector also has a photoelectric transducer disposed at the bottom of crystal and optically connected with each crystal. The light which reaches the transducer is converted into a electrical signal indicative of the intensity of luminescence, i.e., the intensity of radiation impinging upon the scintillation crystal. However, the above described reflection and long path travelled by the reflected light causes a certain loss of optical energy. Also each detector includes a partition opaque to radiation juxtaposed between adjacent crystals to prevent incident radiation and scattered radiation from producing cross talk between the adjacent crystals.

To obtain a high resolution image of the body slice, it is essential that each detector is arranged with as small pitch as possible relative to the fan-beam emerging from the body in order to increase the sampling pitch of the detector array. Further, it is necessary to minimize the dimension of crystal in the fan-beam direction. Otherwise, there occurs a problem that the output signal of detector is reduced because the light receiving area of the photoelectric transducer is diminished. In that event, it is necessary to expose the patient to a larger radiation dosage in order to collect enough information for image reconstruction.

SUMMARY OF THE INVENTION

Accordingly, an object of the present invention is to provide a noval computerized tomography apparatus which includes an array of detectors exhibiting high conversion efficiency in converting incident radiation into electrical signals.

Another object of the invention is to provide a novel computerized tomography apparatus including an array of a large number of very small detectors packed very closely together to yield an accurate, high resolution tomographic image.

These and other objects are achieved according to the invention by providing a novel computerized tomography apparatus including an array of detectors in the form of an array of scintillation crystals upon which fan-beam x-ray radiation impinges, wherein a photodiode is disposed between each of the adjacent scintillation crystals and is optically connected with each crystal. The detection area of each photodiode is elongated along the incident direction of radiation. The luminescence is received by the photodiode, which is elongated parallel to the incident direction of radiation, with a wider area for reception of the luminescence and a shorter path for arrival thereto. The area connected with the crystal and the photodiode does not depend on the sampling pitch of the array of detectors.

Therefore a large number of such detectors with high conversion efficiency can be packed very closely together in an array that will yield a high resolution tomographic image.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
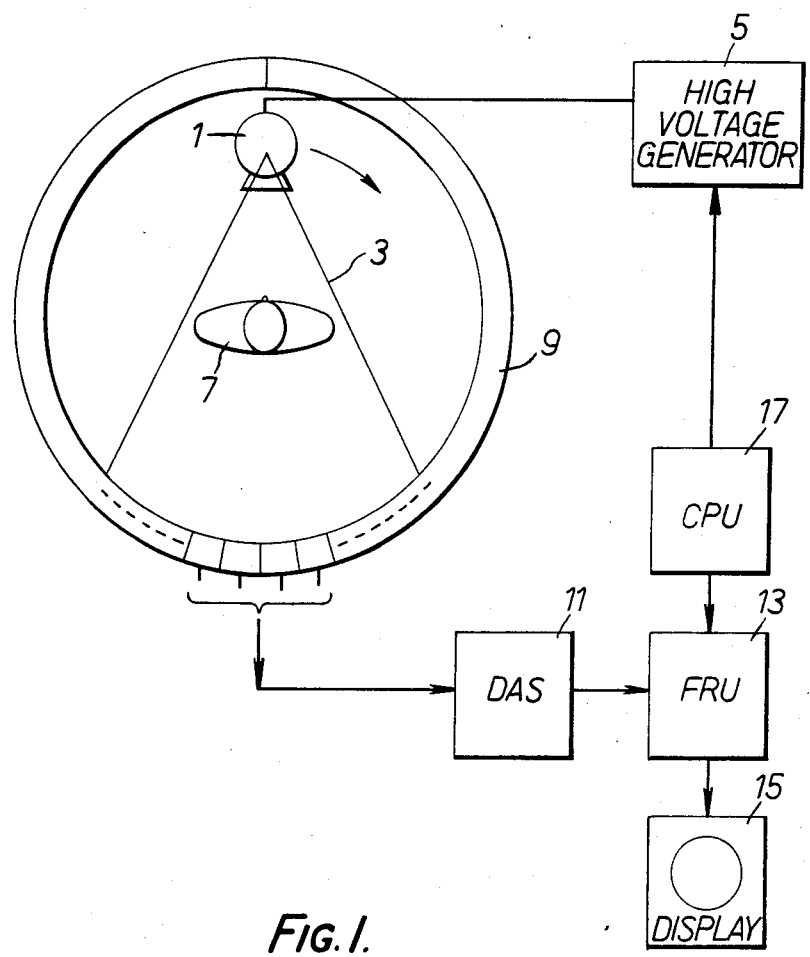
FIG. 1 is a schematic block diagram of a computerized tomographic apparatus in accordance with the present invention.

Referring now to the drawings, wherein like reference numerals designate identical or corresponding parts throughout the several views, and more particularly to FIG. 1 thereof, FIG. 1 shows a computerized tomographic apparatus, which includes a radiation source that rotates around a body 7. High voltage generator 5 supplies pulsed or continuous high voltage power to a rotating radiation source 1. The radiation source 1 irradiates a thin fan beam 3 towards a patient body 7. An array of detectors 9, shown in more detail in FIG. 2, that is a stationary arc is disposed surrounding the patient body which is positioned towards a center of the array. The detectors 9 that are positioned opposite the source 1 receive the fan beam 3 that passes through the patient 7. Each detector 9, which includes a scintillation crystal and photoelectric transducer, converts the radiation impinging thereon into an electrical signal related to the intensity of the radiation. Each electrical signal produced as a result of the detection of radiation is supplied to a Data Acquisition System (DAS)11. Each electrical signal represents an analog quantity related to the intensity of the beam impinging upon the respective detector. DAS 11 collects the electrical signals from the detectors that receive the fan beam to produce projection data that is a one dimensional profile of the body slice. The projection data represent both the intensity of the radiation detected and respective position of detection due to the single view of the source from each detector. Further, DAS 11 converts the projection data into digital form to be suited for digital computation and supplies a Fast Reconstruction Unit (FRU)13 with digital projection data. FRU 13 includes a corrector, a convolver and a back projector (not shown). The corrector corrects the projection data derived from DAS 11, for example, to compensate for the beam hardening of the radiation caused by passing through the body tissue. The convolver convolves the projection data corrected by the corrector. The back projector repeats the back projection of the convolved projection data successively supplied from DAS 11. In such a way, FRU 13 performs the correction, the convolution and back projection for the projection data at different views at least spanned above 180° rotation of the source 1 and a two dimensional image of the body slice. This reconstructed image is visually displayed by the display 15. CPU 17 correlates the rotation of source 1 with the timing of the pulsed high voltage power supplied from the generator 5 or the sampling timing of the detection by the detectors 9 and DAS 11. Also CPU 17 controls the tansfer of the projection data from DAS 11 to FRU 13, from corrector to convolver from convolver, to back projector and so on.

Figure 2:
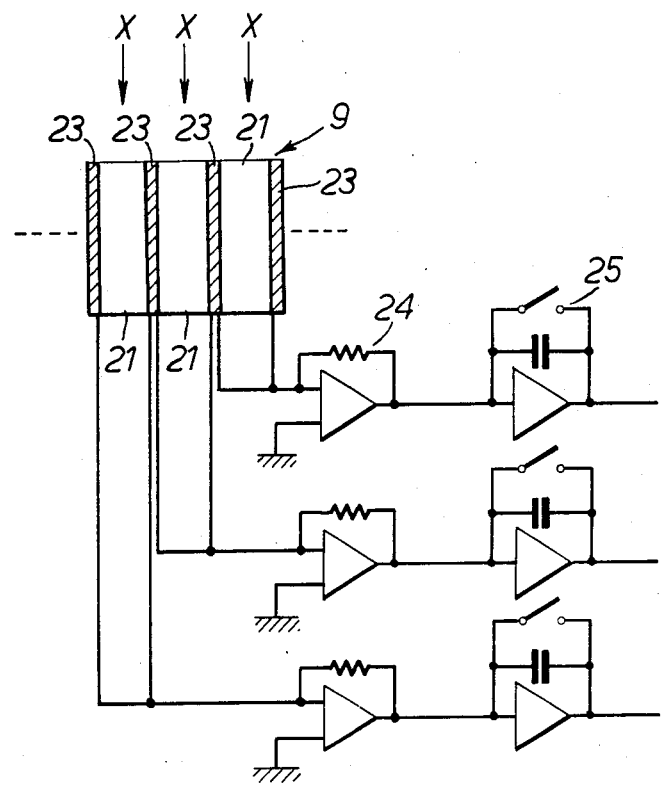
FIG. 2 is a schematic circuit diagram of a part of an array of detectors in accordance with the present invention.

FIG. 2 shows a portion of the array of detectors 9 and the first stage of DAS 11 connected thereto.

Shown in FIG. 2 is a detector array 9 for sensing incident radiation X. This array 9 includes plural scintillation crystals 21 optically coupled to adjacent photoelectric transducers 23. Each scintillation crystal 21 is a means for converting the incident radiation x-ray impinging into a lower spectral band of energy, for example, in the visual region. In the preferred embodiment, it is desirable that the crystal for example a cadmium tungstate (CdWO4), a zinc tungstate (ZnWO4) and so on, has a short decay constant or less afterglow, because time intervals between samplings of the DAS 11 are short for fast reconstruction of the tomography. A long decay of scintillation affects subsequent scintillations, and probably causes DAS 11 to produce incorrect projection data.

Figure 3:
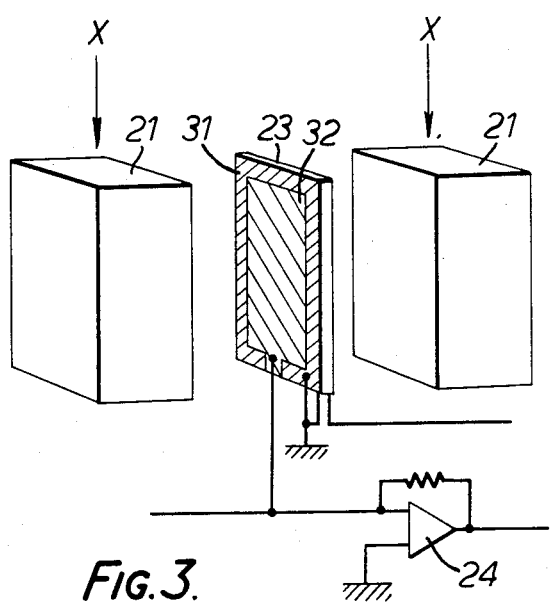
FIG. 3 is an exploded perspective view of a detector in accordance with the present invention.

The photoelectric transducer 23 is optically coupled to a side wall of the crystal 21, shown in more detail in FIG. 3. The side wall of the crystal 21 attached to the photoelectric transducer 23 is parallel to the direction of incident radiation X and transverse to a direction of the array of detectors 9. In the array 9, the crystals 21 and the photoelectric transducer 23 are alternately disposed, with the transducer 23 sandwiched between adjacent crystals 21. Each photoelectric transducer 23 is a photodiode such as a thin doped silicon P-N junction photodiode. In the preferred embodiment, the photodiode 23 is a double surface barrier type which generates independent outputs upon reception of light by each surface. The outputs from the photodiodes whose surfaces are opposite to a crystal 21 are summed to increase the conversion efficiency of luminescence of scintillation into electrical signal, whereby the area sensitive to light is substantially doubled. Further, the array using such a photodiode has a wider incident surface of radiation because the photodiode is thin.

The incident x-ray radiation causes crystal 21 to luminescence. Light from such a luminescence emanates in all directions. Thus, a portion of the light that arrives at surface of photodiode 23 is detected and converted into electrical current signals related to the luminescence. The electrical signals supplied from a pair of photodiodes 23 whose surfaces sandwich the same crystal 21 are summed and the resultant sum which is, of course, an electrical analog current, is supplied to an input of each operational amplifier 24 of DAS 11. The operational amplifier converts the analog current signal into an analog voltage signal and supplies it to an integrator 25. The integrator 25 integrates the voltage signal during a predetermined period. The output of the integrator is fed to an A/D convertor (not shown).

Such an operation is performed for each detection of the array 9 for each irradiation by source 1. Projection data that represents a linear shadowgram of the body slice at one view is organized by the DAS 11.

FIG. 3 shows an exploded perspective view of a part of the array of detectors 9. The photodiodes 23 sandwich scintillation crystals 21. The surfaces of the crystals 21 except for incident surface of x-ray radiation and opposite sides coupled with photodiodes 23 are coated wtih a material that acts to reflect the internal light of luminescence. Some paths of light reflected by this light reflective material arrive at the photodiode 23. But almost all light paths reach the photodiode 23 directly without loss due to reflection.

The photodiode 23 is optically connected with a crystal surface that is not coated with light reflective material. The photodiode 23 and crystal 21 is secured together by a relatively pliable transparent adherent material. The photodiode 23 is caused to exhibit photoconductive effect by the visual or near visual light. This effect is evidenced by a no load potential between layers of layered arrangements of certain semiconductive materials. Incident light causes a migration of electrons between the lattices of layered materials resulting in an excess in one lattice and a deficit in another. This causes a no load potential difference between layers.

In preferred embodiment, the photodiode 23 is a double surface barrier N type silicon diode whose opposite planar surfaces are both vaporized with gold (Au) and aluminum (Al). The region 31 vaporized with Al forms ohmic contact layers with silicon. The region 32 vaporized with Au and encompassed by the region 31 forms P-N junction layers with the silicon. The P-N junction layers are sensitive to incident light, which causes photoconductive effect between the layers of the P-N junction. As a result, a voltage difference arises across the P-N junction layers, and a current related to the intensity of luminescence is obtained from these layers.

The N type silicon diode 21 is sensitive to radiation such as x-rays or gamma-rays and directly converts radiation impinging thereon, irrespective of energy conversion by the scintillation crystal 21. In this diode 23, therefore, the conversion efficiency of radiation into current is higher than that of other diodes not exhibiting direct energy conversion.

There are a many variations in computerized tomography systems. For example, third-generation scanners that rotate both the x-ray source and detectors array synchronously around the patient, fourth-generation scanners that rotate only the x-ray source around the patient and have a stationary arc of detectors at least spanning 180° plus the angle of fan beam in inner or outer orbit of source, and so on are known. Also there are many reconstruction methods and apparata suited for such methods, for example, filtered back projection reconstruction methods with reordering of the fan beam into sets of parallel beam, or without reordering source of the fan beam or detector fan beam into sets of parallel beams. This invention, of course, is applicable to the abovementioned apparata.

Although the present invention has been described with a certain degree of particularity. It should be understood that the present disclosure has been made only by way of example and that numerous changes in the detail of construction, and the combinational arrangement of parts, elements and components can be resorted to without departing from the spirit and scope of the present invention. It is therefore to be understood that within the scope of the appended claims, the invention may be practiced otherwise than as specifically described herein.

What is claimed as new and is intended to be secured by Letters Patent is:

1. A computerized tomography apparatus for examining a slice of a body with radiation, comprising:
    means adapted for irradiating a fan beam of radiation through the body to be examined;
    means adapted for effecting relative angular displacement between the fan beam of radiation and the body;
    means adapted for detecting the radiation that has passed through the body, said detecting means disposed at plural angularly spaced positions to receive at least some of fan beam emerging from the slice of the body and producing signals indicative of the intensity of radiation impinging thereon;
    means for processing said signals to reconstruct an image of said slice;
    said detecting means including scintillating means and photoelectric transducer means alternately disposed in the direction of angular displacement of said fan beam to receive said fan beam, said scintillating means having elongated side walls which define a maximum dimension thereof and provided for converting the radiation impinging thereon into visual or near visual luminescence, each said photoelectric transducer means having an elongated optical connection region extending adjacent and facing an elongated side wall of at least one of said scintillating means for converting said luminescence into an electrical signal, said optical connection region being elongated in the direction of the fan beam to be detected.

2. A computerized tomography apparatus according to claim 1 wherein said detecting means includes pairs of said photoelectric transducer means which sandwich each of said scintillating means, and each said pair of said photoelectric transducer means has outputs electrically combined to define a respective channel.

3. A computerized tomography apparatus according to claim 1 wherein said photoelectric transducer means includes a double surface barrier N type silicon diode having opposed surfaces independently sensitive to radiation impinging thereon.

* * * * *